United States Patent [19]

Laird

[11] Patent Number: 4,575,486

[45] Date of Patent: Mar. 11, 1986

[54] PROCESS FOR DIFFERENTIATING THE ORIGIN OF PARTICLES IN URINE

[75] Inventor: Cleve W. Laird, Simi Valley, Calif.

[73] Assignee: International Remote Imaging Systems, Inc., Chatsworth, Calif.

[21] Appl. No.: 545,760

[22] Filed: Oct. 26, 1983

[51] Int. Cl.$^4$ ......................... G01N 33/50; C12Q 1/02
[52] U.S. Cl. .......................................... 435/7; 435/29; 436/519; 436/520; 436/804; 436/811
[58] Field of Search .......................... 435/7, 29, 34, 39; 436/519, 520, 547, 800, 811, 804

[56] References Cited

PUBLICATIONS

Hanson et al., Lancet, 1: 226–228 (1976).
Rutecki et al., New Eng. J. Med., 284(19): 1049–1052 (1971).
Bartalos et al., Chemical Abstracts, 94:79565k, (1981).
Marier et al., Chemical Abstracts, 90:119095h, 432 (1979).
"Direct Visualization of a Mucoprotein Component of Urine" by Keith R. Porter and Igor Tamm, *The Journal of Biological Chemistry*, vol. 212, No. 1, Jan. 1955; pp. 135–139.
"Ultracentrifugation Studies of a Urinary Mucoprotein which Reacts with Various Viruses" by Igor Tamm, J. C. Bugher and F. L. Horsfall, Jr. *The Journal of Biological Chemistry*, vol. 212, No. 1, Jan. 1955; pp. 125–133.
"Tamm–Horsfall Urinary Glycoprotein" by A. P. Fletcher, A. Neuberger & Wendy A. Ratcliffe, *Journal of Biochemistry*, vol. 120, 1970; pp. 425–432.
"Tamm–Horsfall Urinary Glycoprotein, The Chemical Composition" by A. P. Fletcher, A. Neuberger & Wendy A. Ratcliffe; *Journal of Biochemistry*, vol. 120, 1970; pp. 417–424.
"Characterization and Spearation of an Inhibitor of Viral Hemagglutination Present in Urine" by Igor Tamm and Frank L. Horsfall, Jr. PSEBM, vol. 74, 1950; pp. 108–114.

*Primary Examiner*—Esther M. Kepplinger
*Attorney, Agent, or Firm*—Limbach, Limbach & Sutton

[57] ABSTRACT

Urinary particulates in a human subject which have been coated with THP is determined to be from the region of the nephron which is above the Henle loop in the nephron where THP is produced. The identification of those particles in the urine sample which had been coated with THP is performed by subjecting the sample to THP antibodies to form THP antibody-antigen complexes. These complexes can be identified by a number of ways, such as visual, fluorescent, etc. By determining the percentage of the total particulates which have the coating of THP, a diagnostic tool for determining renal disorders is disclosed.

17 Claims, 1 Drawing Figure

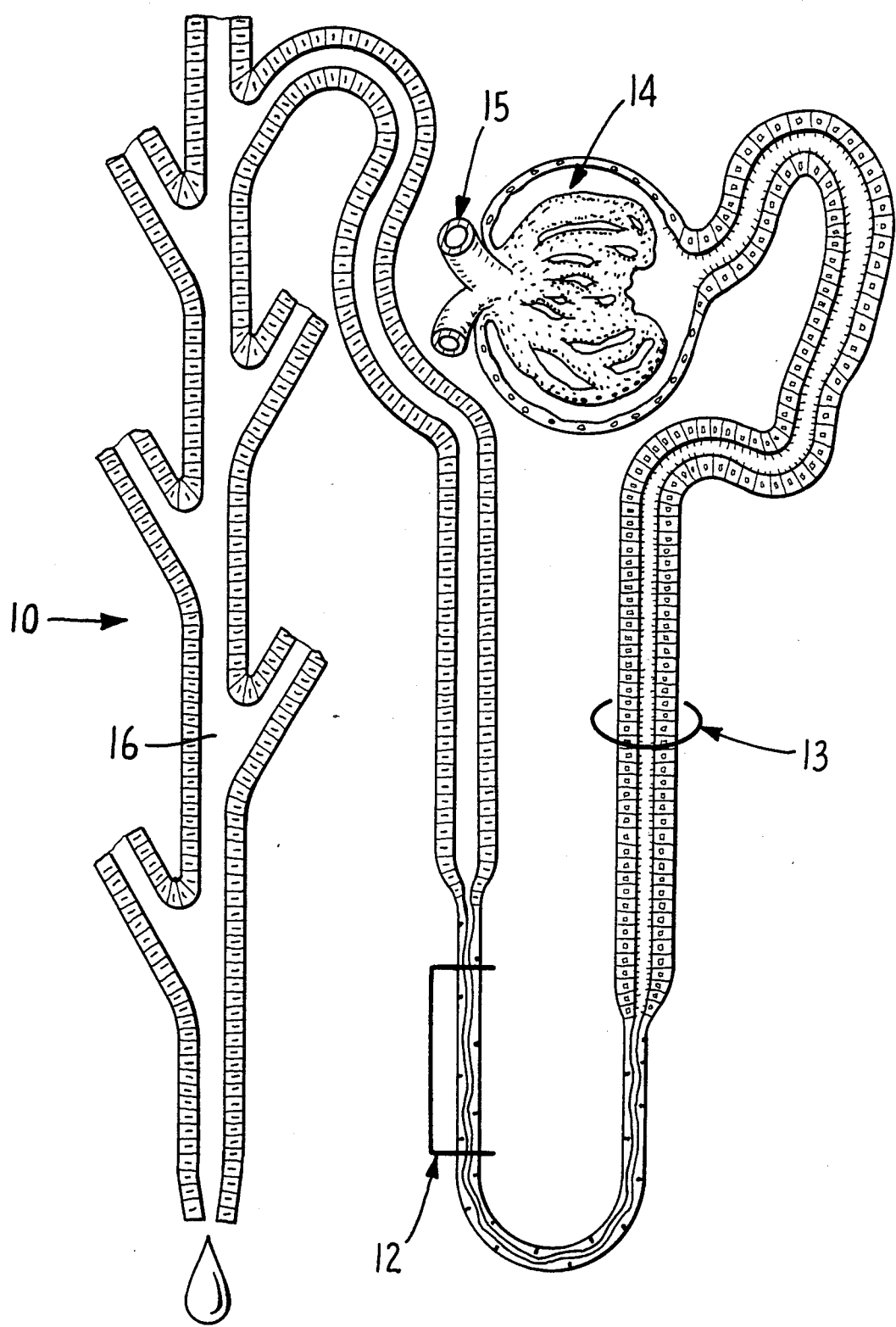

PROCESS FOR DIFFERENTIATING THE ORIGIN OF PARTICLES IN URINE

TECHNICAL FIELD

The present invention relates to a method for determining the origin of particles in urine from a human urinary tract, wherein the tract has a site for producing Tamm-Horsfall Protein (THP). Based upon this method, the number and distribution of urine particulates determined to be from the urinary tract which is above the site for producing THP can be indicative of certain types of renal disorder.

BACKGROUND OF THE INVENTION

THP is a muco-protein which is found in the urinary tract of the human and is well-known in the art. See, for example, "Direct Visualization Of A Muco-Protein Component Of Urine" by Keith R. Porter and Igor Tamm, *The Journal Of Biological Chemistry*, Volume 212, No. 1, January 1955, pages 135-139. See also "Ultracentrifugation Studies Of A Urinary Muco-Protein Which Reacts With Various Viruses" by Igor Tamm, J. C. Bugher and F. L. Horsfall, Jr., *The Journal Of Biological Chemistry*, Volume 212, No. 1, January 1955, pages 125-133. THP is a muco-protein which is produced in the kidneys of a human.

Antibodies for THP are also known in the art. THP antibodies are used to determine the sites of the production of THP in the kidneys. In general, THP is produced only in the distal, convoluted loop of Henele, which is in the kidney. A THP antibody is used to identify those cells that produce THP. In addition, since THP inhibits viral agglutination, THP antibody is used to find THP to inhibit viral agglutination.

Heretofore, when a sample of human urine with urine particulates, such as red blood cell, white blood cell, and cast, are analyzed, it has been difficult to determine the source of origin of these particulates in the absence of casts. Without cast, it is generally difficult to determine where along the urinary tract the urine particulates originate. With the knowledge of the source of urine particulates, it would be possible to determine certain types of disorders. For example, if the white blood cells found in the urine are from the kidneys, then infection of the kidney is suspected. On the other hand, if the white blood cells are not from the kidneys, then the likelihood of infection of the kidneys is remote. Thus, certain types of renal disorders can be diagnosed if the source of the urine particulates can be identified.

SUMMARY OF THE INVENTION

In the present invention, a process for differentiating the origin of urine particulates in a sample of human urine is disclosed. The urinary tract has a site for producing THP. The tract has a portion above the site and a portion below the site. The sample of human urine is mixed with THP antibodies. THP antibody-antigen complexes are then formed. Those particles with the THP anitbody-antigen complex are identified as being from the portion above the site.

BRIEF DESCRIPTION OF THE DRAWING

FIG. 1 is a schematic view of a nephron which is a portion of a urinary tract of a human subject.

DETAILED DESCRIPTION OF THE DRAWING

Referring to FIG. 1, there is shown a nephron 10 which is in a urinary tract of a human subject. The nephron 10 is shown greatly enlarged and is of only the section in the kidney. Along the nephron 10 is a site 12 for the production of THP. This is the distal, convoluted loop of Henle. The portion of the nephron 10, which is above the site 12, for the production of THP is the proximal convoluted tubule 13. Below the site 12 for the production of THP is another portion of the nephron 10, the collecting tubule 16. Above the site 12 are also found the filtration apparatus 15 and Bowman's capsule 14 where the filtrate is collected before passing through the nephron 10.

In the method of the present invention, a sample of urine from a human subject is collected. The sample of urine has urinary particulates, such as casts, red blood cells, or white blood cells. A THP antibody is then mixed with the sample of human urine. The THP antibody forms THP antibody-antigen complexes with those particles in the urine which have THP coated thereon. Those particles with the THP antibody-antigen complexes are then identified as being from the portion of the kidney above the site 12.

The identification of the particles with the THP antibody-antigen complex can be performed in a number of ways. The THP antibody can be labelled with a fluorescent substance, such as fluoroscein. The urine is illuminated with ultraviolet radiation and where the fluoroscein has attached itself to the antibody-antigen complex, it would fluoresce. Then, too, the THP antibody can be labelled with a radioactive substance. Where the particle with the THP has formed a THP antibody-antigen complex, radioactivity would be emitted therefrom. The radioactivity can be converted into visual scintillations and optically detected. Finally, the label to the THP antibody can be visually inspected by a microscope.

The particular THP antibody used to form the THP antibody-antigen complex can be any of the well-known prior art samples. However, in a preferred example, the THP antibody is produced from goat, rather than from rabbit. It is then isolated by well-known physical and chemical techniques. The sample produced from goat is more reactive than the sample from rabbit.

The detection of the source of urinary particles can be used in diagnosis of renal disorder in a human subject. As before, a urine sample containing urinary particulates from a human subject is obtained. The sample of urine is exposed to THP antibody. THP antibody-antigen complexes are formed in the sample. The urinary particulates with the THP antibody-antigen complexes are identified. The portion of the total particulates which form THP antibody-antigen complexes are determined. In the event the portion of the total particulates is significant, then the sample is indicative of the subject having possible renal disorder. As previously discussed, the identification of the THP antibody-antigen complexes can be performed by anyone of visual, fluorescent, or radioactive techniques.

More specifically, a volume of human urine sample containing urinary particulates was analyzed. The urinary sample was first reduced in liquid volume by approximately one-half. This was done merely to increase the concentration of the urine particulates. The two ml volume of urine was reduced to approximately 1 ml by centrifugation and aspiration. 50 ul of THP antibody labelled with fluoroscein was added to the 1 ml volume of urine.

The THP antibody is mixed with the urine by manual vortex action to facilitate the formation of antibody-antigen complexes. The resultant mixture is viewed under white incandescent light to determine the total number of white and red blood cells. In addition, each individual cell is examined under both white and monochromatic illumination to ascertain the presence of THP antibody-antigen complex coating the cells. The total number of cells examined is recorded along with the total number of cells detected which exhibit THP antibody-antigen complex. When the ratio of the complexed antibody-antigen particles to the total particles is significant, then the urine sample is indicative of the subject having a renal disorder.

In a test involving patients with known renal disorders, patients suffering from glomerular nephritis had their urine sample analyzed. These patients had $38\pm7\%$ of their urinary particles coated with THP. For patients with chronic interstitial nephritis, $57\pm10\%$ of the urinary particles were found to be coated with THP.

The present invention is the discovery that particulates which pass through the site 12 for the production of THP in a urinary tract are coated with the THP. Thus, using THP antibodies, THP antibody-antigen complexes can be formed on those particles and those particles can be identified. It has also been discovered that merely exposing the urinary particulates to THP muco-protein does not cause the THP muco-protein to be coated around those particulates. For example, cells that have been bathed in a solution containing THP muco-protein were found not to be coated with the THP muco-protein. In fact even where cells have been incubated in a solution of THP for at least eight hours, they are not so coated. The urinary particulates are coated with THP only by passing through the site 12 where THP is produced. Particles in the portion 16 below site 12, even when mixed with THP from the site 12 in the nephron 10, are not found to be coated with THP. Furthermore, where red blood cells are removed from the filtration apparatus 15 and are not permitted to pass through the site 12, they are found not to have a coating of THP. It is believed that, as the particles from the Bowman's capsule 14 through the proximal convoluted tubule 13 pass through the site 12, somehow the particles are changed to permit the THP to adhere to those particles. Furthermore, it should be noted that the passage of particles through the THP producing region and becoming coated therewith is unique to THP only. For example, albumen from the kidney does not coat those cells from the kidney. Thus, the discovery of cells that pass through the site 12 in the Henele loop as being coated with THP is unique and constitutes a non-obvious discovery, and can be used for diagnosis of various renal disorders.

I claim:

1. A process for differentiating the origin of red blood cells or white blood cells, in urine from a urinary tract, wherein said tract has a situs for producing Tamm-Horsfall Protein (THP) and said tract having a portion above said situs and a portion below said situs; said method comprising the steps of:
   exposing said urine to THP antibodies;
   forming THP antibody-antigen complexes in said urine; and
   identifying those red blood cells or white blood cells, coated with said THP and forming THP antibody-antigen complex as being from said portion above said situs.

2. The method of claim 1, wherein said antibody is labelled with a fluorescent substance, and said identifying step further comprises:
   illuminating said urine with ultraviolet radiation; and
   detecting fluorescent radiation from said urine.

3. The method of claim 1, wherein said antibody is labelled with a radioactive substance, and said identifying step further comprises:
   converting said radioactivity into scintillations; and
   optically detecting said scintillations.

4. The method of claim 1, wherein said identifying step further comprises
   visually inspecting said urine.

5. A method for diagnosing renal disorder in a human subject, comprising the steps of:
   obtaining a urine sample containing red blood cells, or white blood cells, (hereinafter: urinary particulates) from said subject;
   exposing said sample to Tamm-Horsfall Protein (THP) antibody;
   forming THP antibody-antigen complexes in said sample;
   identifying the urinary particulates coated with said THP and forming THP antibody-antigen complex; and
   determining the portion of the total urinary particulates which form THP antibody-antigen complex;
   wherein said portion is indicative of whether or not said patient has a renal disorder.

6. The method of claim 5, wherein said antibody is labelled with a fluorescent substance, and said identifying step further comprises:
   illuminating said urine with ultraviolet radiation; and
   detecting fluorescent radiation from said urine.

7. The method of claim 5, wherein said antibody is labelled with a radioactive substance, and said identifying step further comprises:
   converting said radioactivity into scintillations; and
   optically detecting said scintillations.

8. The method of claim 5, wherein said identifying step further comprises
   visually inspecting said urine.

9. A process for diagnosing renal disorders in a human subject comprising:
   (a) obtaining a volume of urine sample, containing red cells, or white blood cells (hereinafter: urinary particulates) from said subject;
   (b) adding a known amount of a Tamm-Horsfall Protein (THP) specific antibody to the volume of step (a) forming a mixture;
   (c) physically mixing the mixture of step (b) to facilitate the complexing of antibody-antigen;
   (d) determining those urinary particulates which have become associated with the THP specific antibody;
   (e) determining the total number of urinary particulates; and
   (f) calculating the ratio of complexed particles determined in step (d) and total particles determined in step (e);
   wherein said ratio is indicative of whether or not said subject has a renal disorder.

10. The process of claim 9 further comprising the step of decreasing the liquid to urinary particulates ratio by volume of the urine sample.

11. The process of claim 10 step (a) wherein the original volume of urine containing urinary particulates is approximately 2 ml and is decreased by approximately one-half.

12. The method of claim 10, wherein the decreasing step is accomplished by centrifugation and aspiration.

13. The process of claim 9, wherein the THP specific antibody is labelled to facilitate identification of the free and unassociated antibody.

14. The process of claim 13 wherein the THP specific antibody is labelled with a fluorescent substance.

15. The process of claim 14, wherein said fluorescent substance is fluorescein.

16. The process of claim 9, wherein in the event the ratio of complexed THP specific antibody urinary particles to total urinary particles is approximately between 0.31 and 0.45, said sample is indicative of said subject having glomerular nephritis.

17. The process of claim 9, wherein in the event the ratio of complexed THP specific antibody urinary particles to total urinary particles is approximately between 0.47 and 0.67, said sample is indicative of said subject having chronic interstitial nephritis.

* * * * *